United States Patent
Hadvary et al.

(10) Patent No.: US 10,076,356 B2
(45) Date of Patent: Sep. 18, 2018

(54) SUBCUTANEOUS NEEDLE INSERTION MECHANISM

(71) Applicant: PharmaSens AG, Biel-Benken (CH)

(72) Inventors: Paul Hadvary, Biel-Benken (CH); Hansjorg Tschirky, Sissach (CH)

(73) Assignee: PharmaSens AG, Biel-Benken (CH)

( * ) Notice: Subject to any disclaimer, the term of this patent is extended or adjusted under 35 U.S.C. 154(b) by 145 days.

(21) Appl. No.: 14/391,402

(22) PCT Filed: Apr. 8, 2013

(86) PCT No.: PCT/EP2013/057327
§ 371 (c)(1),
(2) Date: Oct. 9, 2014

(87) PCT Pub. No.: WO2013/153042
PCT Pub. Date: Oct. 17, 2013

(65) Prior Publication Data
US 2015/0141776 A1    May 21, 2015

(30) Foreign Application Priority Data
Apr. 11, 2012  (EP) .................................. 12163675

(51) Int. Cl.
*A61B 5/1455*   (2006.01)
*A61B 17/34*    (2006.01)
(Continued)

(52) U.S. Cl.
CPC ........ *A61B 17/3403* (2013.01); *A61B 5/1495* (2013.01); *A61B 5/14503* (2013.01);
(Continued)

(58) Field of Classification Search
CPC ............ A61B 5/14532; A61B 5/14546; A61B 5/1486; A61B 5/14539; A61B 5/0031
See application file for complete search history.

(56) References Cited

U.S. PATENT DOCUMENTS

| | | | | |
|---|---|---|---|---|
| 5,586,553 A | * | 12/1996 | Halili ................ | A61B 5/14532 600/316 |
| 5,591,188 A | * | 1/1997 | Waisman ........... | A61B 17/3472 604/157 |

(Continued)

FOREIGN PATENT DOCUMENTS

| | | |
|---|---|---|
| EP | 2436311 A1 | 4/2012 |
| EP | 2438938 A1 | 11/2012 |

(Continued)

*Primary Examiner* — Eric Winakur
*Assistant Examiner* — Marjan Fardanesh
(74) *Attorney, Agent, or Firm* — Xsensus, LLP

(57) ABSTRACT

A subcutaneous access device has a skin attachment plate coated with an adhesive layer. The skin attachment plate is moveably linked by a retraction mechanism to a needle support with fixedly positioned needles. In the ready-to-use position the skin attachment plate is spaced away from the needle support and covers the fixedly positioned needles. Subcutaneous insertion of the needles is effected by attachment of the skin attachment plate with the adhesive layer to the skin and releasing the retraction mechanism, thus triggering the pulling of the attached skin with high velocity against the tip of the needles.

20 Claims, 9 Drawing Sheets

(51) Int. Cl.
*A61M 5/158* (2006.01)
*A61M 5/142* (2006.01)
*A61B 5/145* (2006.01)
*A61B 5/1495* (2006.01)
*A61M 5/145* (2006.01)
*A61B 17/00* (2006.01)

(52) U.S. Cl.
CPC ...... *A61M 5/1452* (2013.01); *A61M 5/14248* (2013.01); *A61M 5/158* (2013.01); *A61B 2017/00951* (2013.01); *A61M 2005/1585* (2013.01)

(56) References Cited

U.S. PATENT DOCUMENTS

| | | | |
|---|---|---|---|
| 5,931,814 A | 8/1999 | Alex et al. | |
| 6,210,369 B1 * | 4/2001 | Wilmot | A61M 5/2033 604/157 |
| 6,424,847 B1 * | 7/2002 | Mastrototaro | A61B 5/14532 600/316 |
| 7,318,816 B2 * | 1/2008 | Bobroff | A61M 5/158 604/136 |
| 2002/0022798 A1 | 2/2002 | Connelly et al. | |
| 2004/0162521 A1 * | 8/2004 | Bengtsson | A61B 5/150022 604/136 |
| 2006/0200073 A1 * | 9/2006 | Radmer | A61M 5/14244 604/93.01 |
| 2008/0004515 A1 | 1/2008 | Jennewine | |
| 2008/0249471 A1 * | 10/2008 | DeStefano | A61M 5/158 604/157 |
| 2009/0163874 A1 * | 6/2009 | Krag | A61M 5/14248 604/180 |

FOREIGN PATENT DOCUMENTS

| | | |
|---|---|---|
| WO | WO 2004/030728 A2 | 4/2004 |
| WO | WO 2005/063115 A1 | 7/2005 |

\* cited by examiner

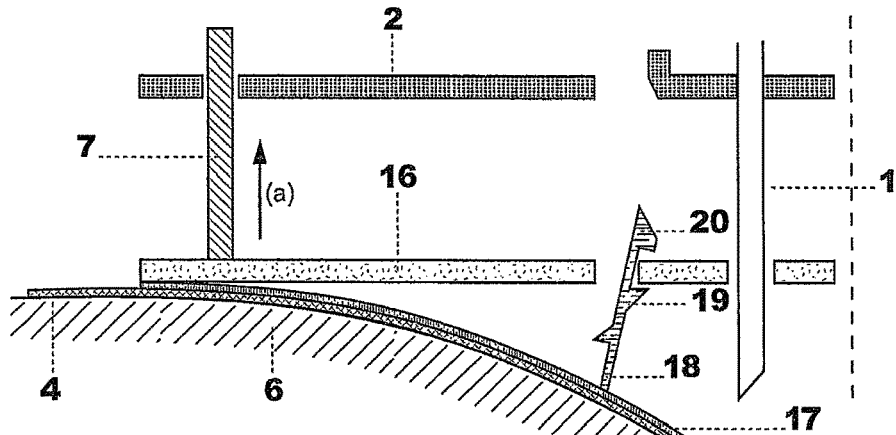
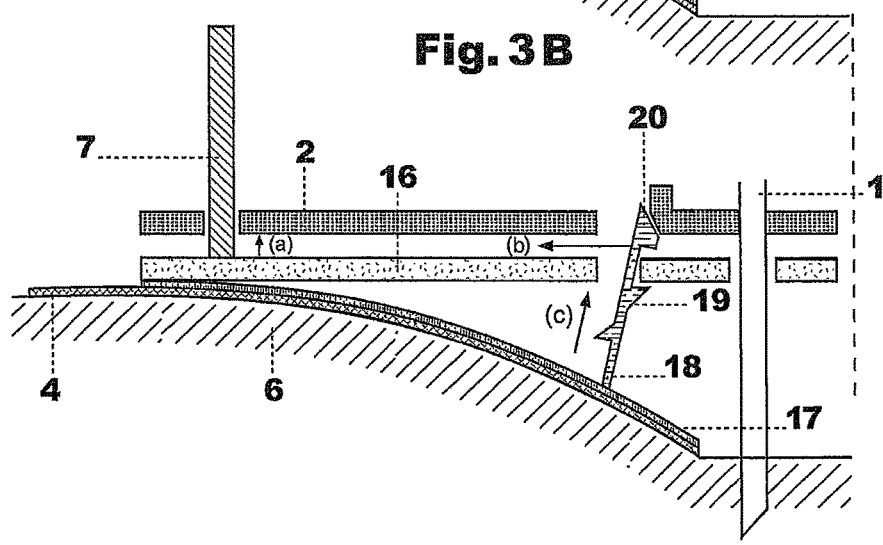
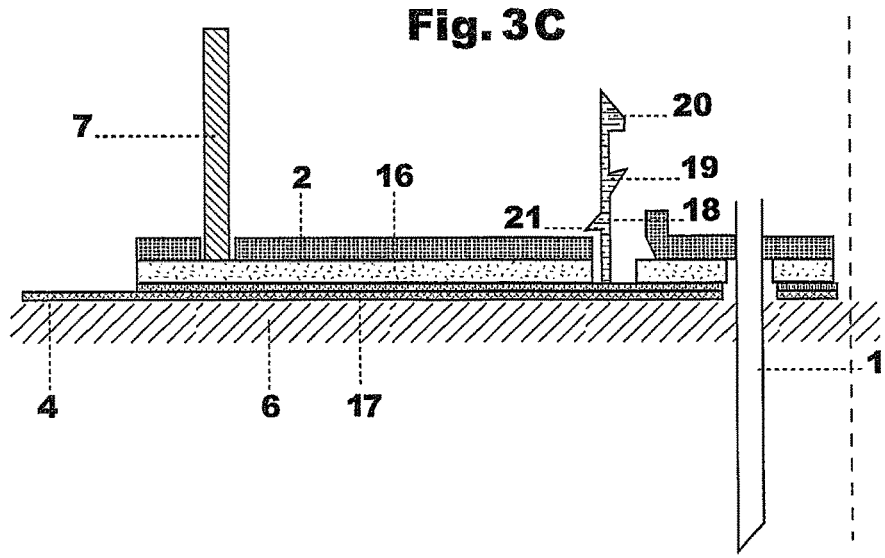

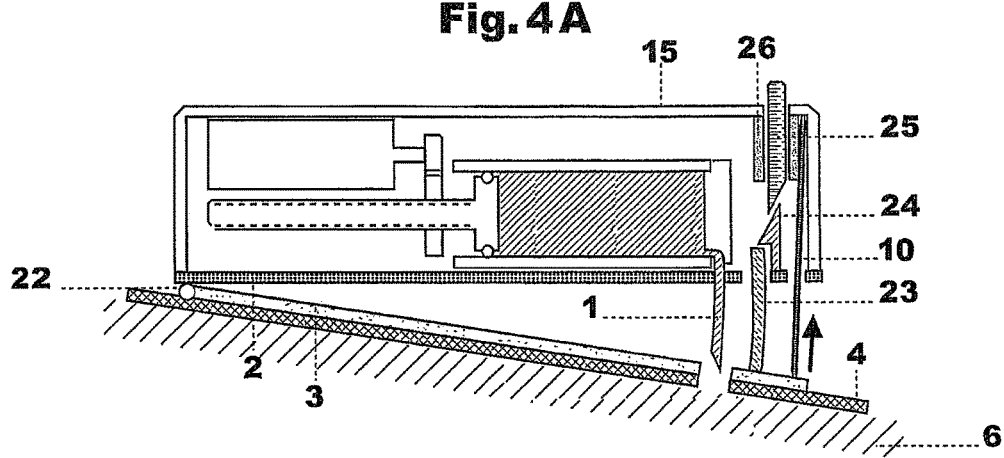
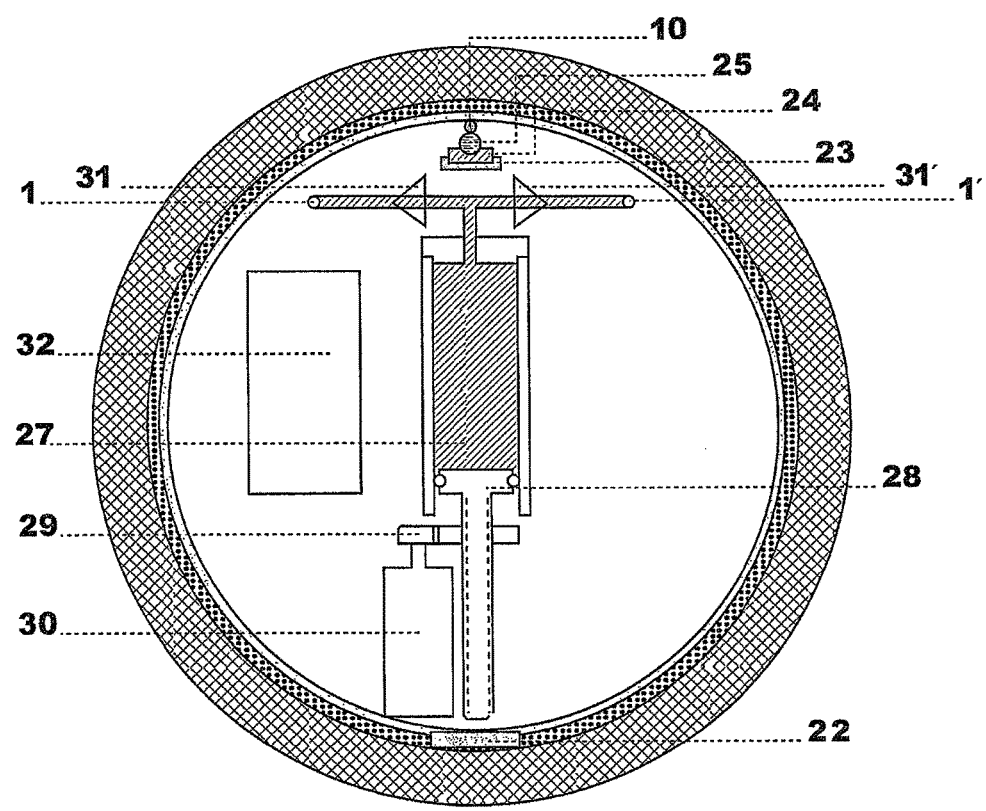

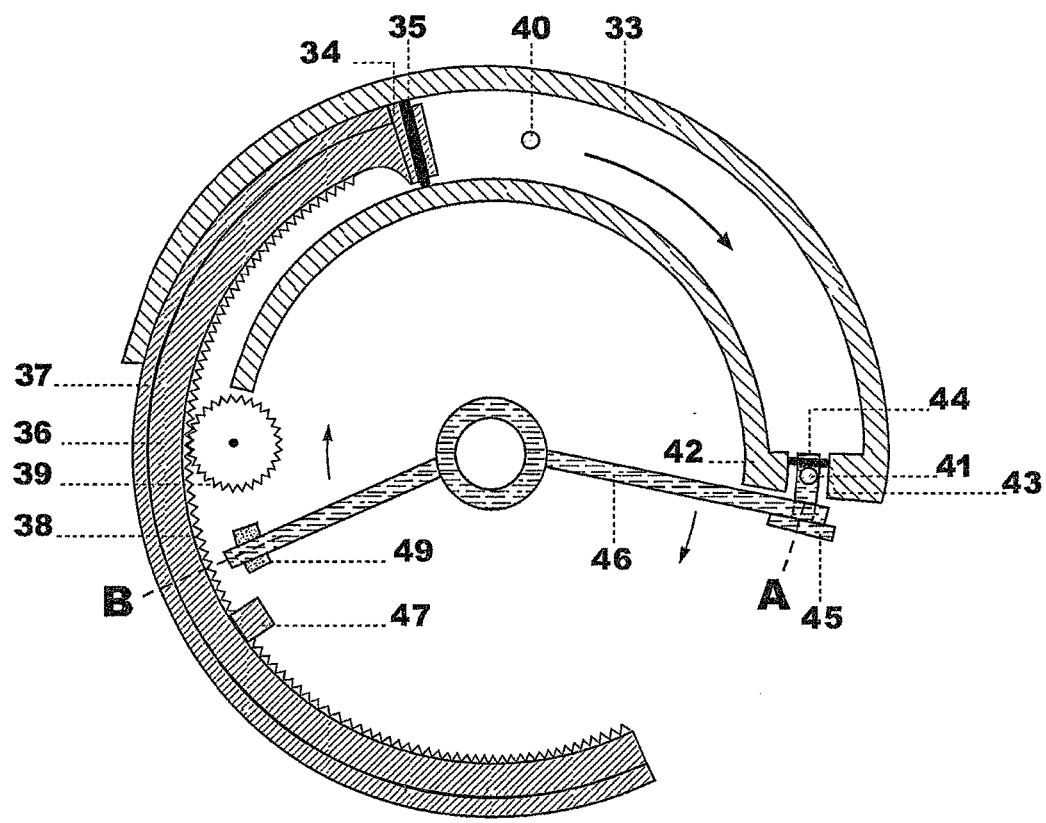
Fig. 5
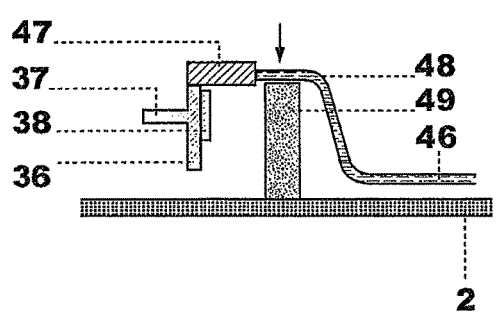
Detail B
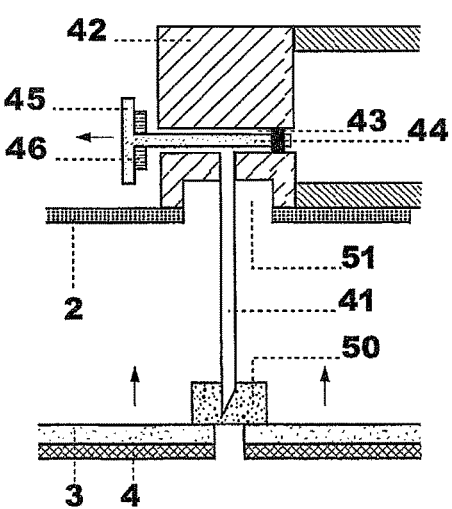
Detail A

SUBCUTANEOUS NEEDLE INSERTION MECHANISM

The present invention is related with a device for subcutaneous access according to the preamble of claim 1.

Fields of application for this type of subcutaneous needle insertion mechanisms is the injection of physiologically active fluid into an individual such as a patient, the access to interstitial fluid for diagnostic purposes and/or for transmitting sensible signals to the individual by means of subcutaneous probes. For this use usually manual insertion of needles into the skin is requested or subcutaneous needle insertion mechanisms are applied shooting the needles into the skin either movably connected to functional elements of devices or needing manual connections after having been placed into the skin.

Patch type devices attached to the skin with such functionalities have been described especially in diabetes care, like insulin infusion and continuous glucose monitoring.

The needles are typically inserted into the skin manually or by separate skin insertion devices. More recently, especially with insulin infusion pumps, skin insertion mechanisms are integrated into the device, shooting the delivery cannula into the skin.

Further, a system with multiple cannulas for infusion being shooted into and removed from the skin consecutively has been described e.g. by R. C. Jennewine in US 2008/0004515, to avoid the interference from tissue reactions.

Shooting several needles with different functionalities and separate placement into the skin with separate skin insertion mechanisms is a technical challenge and problematic for safe operation, especially with the preferred small size of patch type devices, with preferentially miniaturized needles, and the desire to combine the different functionalities within the same device, e.g. monitoring glucose levels and injection of insulin. In particular the need for establishing connectivities after insertion into the skin or having flexible connections between the functional components located fixedly in the device, like the pump or analyte monitoring system with the cannula or subcutaneous monitoring probe being shooted into the skin is a disadvantage of known devices, adding complications in handling and being prone to faults. Therefore, many devices still relay on insertion of fixedly positioned needles into the skin manually, with the disadvantage of patient's aversion, problematic guidance of miniaturized needles, and a mostly insufficient insertion velocity which is not very reliable and need relatively long needles for safely piercing the skin.

An appealing solution to avoid the need to have a flexible connection between the subcutaneous delivery cannula and the injection pump system has been described in U.S. Pat. No. 5,931,814, disclosing a construction with a device attached at its periphery to the skin by an adhesive and using a central cannula fixedly connected to the pump-reservoir, projecting axially beyond the underside of the device casing and a movable protective element surrounding the cannula which is, in a first position, pushing the skin back from the tip of the cannula and in a second position is retracted into the device thereby exposing the tip of the cannula to the skin which by relaxation from the stretched state accelerates sufficiently to be penetrated by the cannula. The skin insertion by the disclosed systems relies on a high elasticity of the skin, which is not necessarily sufficient with elderly patients and the relaxation speed of the skin limits the functioning to very thin needles with very sharp tips for effecting skin penetration by the tip of the needle, implying severe limitations and a significant safety concern.

An improvement of this paradigm for needle insertion into the skin has been described in WO 2005/063115 for diagnostic analyte monitoring devices which also improves safety of skin penetration in patients with reduced elasticity of the skin using as skin insertion mechanism a flexible, pre-stretched bottom of the device with a central opening and having the skin attached by an adhesive to the entire surface of this flexible surface, most importantly extending also to close vicinity to the needle: thus, upon relaxation of the pre-stretched bottom the attached skin is actively pulled against the tip of the needle.

In spite of the attractiveness of this concept for skin insertion of needles it has drawbacks if applied to the insertion of a non-centrally located needle, or for multiple needles at different locations. In addition, the mechanism using a stretched bottom of the device in the form of a cone with a central opening for the needle severely limits the injection depth relative to the device diameter. The subject invention does not have these limitations in and even allows the insertion of needles at a certain angle, e.g. of 45°, differing from the restriction to perpendicular insertion by known insertion mechanisms based on this principle.

The aim of the present invention is to provide a solution allowing safe and easy insertion of one or several needles simultaneously into the skin, not being dependent on the central location of the needle, and avoiding other disadvantages of the state of the art needle insertion mechanisms.

According to the invention this is achieved by a subcutaneous access device of the initially mentioned kind with the characterizing features defined in the body of claim 1.

The configuration using a movable skin attachment plate coated with an adhesive surface which pulls the attached skin against the tip of the needles for subcutaneous implantation solves the problem to achieve the insertion of several needles fixedly connected to functional elements of a device. Further, the insertion depth is independent on the diameter of the device and can therefore be well above five millimeters even with small patch-type devices, but also very small insertion depths of about one millimeter can be reliably achieved. In addition the insertion of fixedly connected needles which are being positioned remote from the center of the device and needle insertion at an angle different from perpendicular is solved according to the subject invention by the subcutaneous needle insertion mechanism having the features disclosed herein below.

For the purpose of this specification certain terms are used with the following definitions.

Adhesive layer is composed of three parts, glue for fixing to a skin attachment plate, a textile providing the necessary flexibility and a glue for fixing onto an individual's skin. Suitable materials for temporary wearing on the skin with strong adhesive properties and minimal allergenicity are commercially available. This adhesive layer is fixed on the skin attachment plate preferentially using a surface which is significantly smaller than the surface attaching to the skin. This can be accomplished e.g. by an adhesive layer extending beyond the surface of the skin attachment plate or if a shape for the adhesive layer similar to or only slightly larger than the surface of the skin attachment plate is chosen, by fixing the adhesive layer to the skin attachment plate in such a way that an outer annular zone is not fixed to the skin attachment plate. Such a design is described in EP0825882 for a medical device with a rigid base.

Analyte means any endogenous or exogenous substance the concentration of which can be used to diagnose the health, organ function, metabolic status, or drug metabolizing capacity of an individual. Examples of endogenous substances are glucose, lactate, oxygen, creatinine, etc. Examples of exogenous substances are drugs, metabolites of such drugs, diagnostic substances (e.g. inulin) etc.

Analyte determining system comprises all elements necessary for determination the concentration of analytes in subcutaneous tissue. Contacting of subcutaneous tissue is achieved via diagnostic probes with their active surface inserted into the skin. The detection system specific for the targeted analytes can be in direct contact with the subcutaneous tissue e.g. as sensors being part of the diagnostic probes or indirectly, e.g. via the dialysis fluid from a microdialysis probe. The signals generated by the detection system are converted to quantitative analyte concentration values and displayed on the device and/or transmitted wirelessly to a display unit and/or used for the controlled delivery of injection fluid and/or for transmitting signals for averting the patient of analyte concentration values outside of a pre-defined range.

Depending on the type, requested precision and implantation duration of the active surface of the diagnostic probe, the analyte determining system might require a periodic calibration. Periodic calibration can occur by direct input of externally generated calibration values, e.g. for glucose by the concentration measured in fingerprick-blood. Alternatively, the analyte determining system can include a calibration system periodically exposing the analyte determining system to a calibration fluid with known analyte concentration. Since during calibration no analyte determinations can be done, a tandem system with two analyte determining systems having diagnostic probes placed spaced from each-other and operated alternatively might be necessary for in-situ calibration to bridge the wash-out and diffusion-away time following introduction of calibration fluid.

Calibration system periodically exposes the detection system to known analyte concentrations. This can be achieved e.g. by a pump system, delivering a calibration fluid with known analyte concentration to the detection system. If the detection system is in direct contact with the subcutaneous tissue e.g. by sensors being part of the diagnostic probes, the calibration fluid can be delivered in-situ by a cannula having its orifice close to the sensor.

Control elements contain all necessary electronics and software components for all necessary functions of the device like, but not limited to, initiating, controlling and surveying the correct functioning of the device, control of delivery of injection fluid according to internal or external signals, feeding and controlling the analyte determining systems and transforming sensor signals into analyte measurements, storing, displaying and transmitting analyte measurements online or batch-wise, interacting with external control devices, preferentially wirelessly, and actuating signaling to the patient by means of inbuilt probes transmitting signals subcutaneously and/or external systems of notification to the patient if the device is not functioning properly or if analyte measurements are not within a predefined range. The control elements allow also to operationally linking the multiple functions of the device.

Delivery of injection fluid encompasses both relatively fast injection (bolus) and relatively slow introduction (also called infusion or instillation) of a liquid into the body. A pump for delivery of injection fluid, such as e.g. insulin can be any combination of reservoir and delivery mechanism as known in the prior art, such as, but not limited to, syringe-type pumps, peristaltic pumps, piezoelectric pumps or consisting of a flexible reservoir squeezed by mechanical, pneumatic or hydraulic means. A cannula for the delivery of injection fluid into the skin is preferentially fixedly positioned and connected to the pump.

In order to avoid granulomatous response to the injection fluid at the injection site upon prolonged delivery of injection fluid, like e.g. with insulin, leading to slower resorption of the injection fluid, multiple cannulas situated distant from each-other in the skin, can be connected to the same pump, being actuated sequentially for delivery of the injection fluid.

For high precision of delivery combined with a small footprint of the device, preferentially a circular syringe pump with a toroidal barrel is used.

Diagnostic probe is a functional element for the determination of analyte concentrations and means, but is not restricted to, any sensor, body fluid removal or microdialysis probe. The diagnostic probe is partially inserted into the skin and at least its active surface, located close to the inserted tip is in direct contact with the subcutaneous tissue. In case that a diagnostic probe is inserted into the skin by means of a guide needle, this guide needle is preferentially only partially retracted following insertion into the skin, as far as needed for exposing the active surface to the subcutaneous tissue. Only partial retraction of the guide needle has the advantage that connecting lines of the diagnostic probe to the other elements of the analyte determining system have not to be interrupted for guide needle removal, or, alternatively the guide needle has not to have a slit allowing removal: such a U-shaped guide needle necessitates guide needle diameters well above 0.5 mm which cause painful skin insertion since further miniaturisation would lead to sharp, tissue-cutting edges of the U. In contrast, only partial retraction without removal of the guide needle allows its miniaturization down to about 0.2 mm diameter.

Display and interactive communication means can be inbuilt on the device, e.g. an LCD display and keys for entering commands, or a separate entity linked by wireless communication with the device.

Functional package is designed to hold the skin insertion mechanism or device by a releasable coupling mechanism and has a peel-off cap to protect the sterility and to keep the active surface of diagnostic probes during storage in a defined environment, such as humidity. The functional package has also a rim element allowing, after removal of the cap, the correct attachment of the rim of the adhesive layer by pressing all-around against the skin. Further, the functional package protects the release/start mechanism against premature, unintended operation and the release/start mechanism can be actuated only following attachment of the device to the skin and removal of the functional package. In addition, in case that the skin insertion mechanism can or device is composed of a reusable part and a disposable part, the functional package can have features facilitating and securing correct assembly and disassembly.

Means for determination of microdialysis recovery in the microdialysate can e.g be a sensing system for determination of the recovery in the microdialysate of an indicator added to the dialysis fluid. The magnitude of decrease in concentration is indicative of the microdialysis recovery. Across the dialysis membrane of the microdialysis probe analytes with a limited molecular mass can pass in both directions and under non-equilibrium conditions the percentage recovery at the other side of the membrane is dependent on factors such as pore-width of the dialysis membrane, molecular size of the analyte, geometry of the probe, pumping speed of the dialysis fluid, etc. Preferentially, an indicator substance is chosen which is not present in the subcutaneous tissue and has physicochemical properties similar to the analyte to be determined. One possibility is to use the ionic reference technique as described e.g. by Trajanoski et al. in Diabetes Care 1997; 20:1114-1121 for determination of glucose recovery by microdialysis in adipose tissue.

Microdialysis probes have a dialysis membrane as active surface forming the interface between the subcutaneous fluid and a dialysis fluid which is passed at the inner side of the membrane. In a preferred embodiment a microdialysis probe consists of an inner and an outer tube which is covered at the implantable part close to the tip by a dialysis membrane. The inner tube is connected to a pump which delivers the dialysis fluid and the outer tube, as outlet for the dialysate is connected to an analyte determining system which can further comprise means for determination of microdialysis recovery. Alternatively, the outlet for the dialysate can be connected to a microdialysate collection system collecting samples for determination of analytes external to the device by, but not limited to biochemical, immunological, HPLC, or LC/MS/MS methods. The samples can be collected in separated receptacles or in a continuous cavity, e.g. a tube or barrel taking precautions that mixing of samples taken at different times is reduced to a minimum. This can be achieved by means for segmentation of the microdialysate in the continuous cavity by introduction of segments of gas, e.g. air bubbles or of a fluid non-miscible with the aqueous dialysate e.g. an oil droplet to separate the dialysate into individual fractions and therewith avoiding longitudinal mixing.

Needles are functional elements with a tip being configured and being rigid enough to allow easy piercing the patient's skin and penetration into the skin. Insertion into the skin can be achieved in a minimally invasive and painless way if the diameter of the needle is very small, preferentially below 0.3 mm. These needles include, but are not restricted to, hollow needles such as cannulas for introducing an injection fluid, tubes or solid needles as diagnostic probes or tubes as guide needles for introducing flexible diagnostic probes, or tubes or solid needles for transmitting signals subcutaneously.

If the needle has the function of a guide needle for subcutaneous insertion of a diagnostic probe, the guide needle can be completely removed or preferentially only partially retracted. The guide needle is partially retracted by a mechanism ensuring that retraction is actuated only consecutively to completed insertion of the guide needle into the skin, and the guide needle is retracted as far as needed for exposing the active surface at the tip of the diagnostic probe to subcutaneous tissue, but without interfering with fixed connections between the active surface and the other elements of the analyte determining system.

Needle support enforces the fixed positioning of the needles and has constructional features allowing a directionnally guided movement of the skin attachment plate relative to the needle support by the retraction mechanism. During the needle insertion the needle support is fixedly connected to the device body which comprises the device housing and all the functional units necessary for treatment and diagnostic purposes etc. After the needle insertion the needle support may be disconnected from the device body.

Probes transmitting signals subcutaneously to the patient can become activated if an action of the patient is required, e.g. by measured analyte levels or changes surpassing predetermined limits, failure or malfunction of components, e.g. of delivery of injection fluid or of diagnostic probes. The signals are preferentially tactile stimuli, such as e.g. mild electrical impulses, changes in temperature, or vibration. For alerting the patient, mild electrical impulses transmitted directly to the subcutaneous tissue by electrodes inserted into the skin increase the safety of being recognized and decrease the necessary signal-intensity, interindividual variability and distraction by environmental stimuli.

Release element de-blocks the withholding means which are e.g. pre-stressed by a spring-type mechanism and thus actuates the retraction mechanism. The construction of the release element and of the withholding means is complementary, e.g. if the withholding means are using hook-type components for blockage, the release element can have protruding pin-shaped components releasing blockage by the hook-type components.

Retraction mechanism linking the skin attachment plate to the needle support is movable from a first position in which the skin attachment plate and the needle support are removed from each-other to a second position in which skin attachment plate and the needle support are close to eachother. It is configured such that in the ready-to-use first position the skin attachment plate covers the tip of the needles and upon actuation of the retraction mechanism effects subcutaneous insertion of the needles by pulling the skin, attached by the adhesive surface, towards the needle support, against the tip of the fixedly positioned needles. Diverse embodiments and functionalities of the retraction mechanism are further exemplified in the description of the skin attachment plate.

Preferentially, the retraction mechanism is a spring-type mechanism comprising a spring for rapidly pulling the skin attachment plate against the needle support and guideways to ensure a smooth and directionally well-defined movement. In the ready-to-use position, the spring type mechanism is stressed and the skin attachment plate is held in a position sufficiently spread away from the needle support, by withholding means, to conceal the needles and protect them from contacting the skin even if the skin attachment plate is pushed manually against the skin of the patient (position 1). Upon actuation of a release element, e.g. by means of a sliding bolt or hook-type mechanism, the withholding means are released and the skin attachment plate can shoot from position 1 to a position in which it is touching the needle support (position 2). The retraction mechanism exerts sufficient velocity and force for implantation of the needles by pulling the attached skin against the tip of the needles, thus piercing the skin and completely inserting the implantable portion of the needles into the skin.

Alternatively, other drives for, or kinds of retraction mechanisms, like e.g. electromechanical or pneumatic drives or telescopic guideways as known in prior art, can be employed.

The retraction mechanism is preferentially integrated into a device, which includes all elements for the intended application. Such devices are spanning from simple devices like e.g. injection pens to highly integrated patch-type closed-loop infusion devices controlled by diagnostic analyte sensing systems.

Alternatively, it can also be configured in such a way that following needle insertion, most parts of the retraction mechanism can be removed. Such a construction is preferential if the skin insertion mechanism is being used only skin-attached subcutaneous infusion ports, inserting needles which are then connected to a remote device. Such an example can e.g. be an infusion set connected to an external insulin pump by a tube by means of a connecting system, like a septum or a Luer lock. Removal of most parts of the retraction mechanism allows reducing the size of the skin-attached infusion port for optimal patient comfort.

Sensors have an active surface which provides some signal (e.g. electrochemical, optic, sonar, thermometric, surface plasmon resonance, piezoelectric or magnetic) according to the concentration of the analyte. Sensors can be directly exposed to the subcutaneous tissue as part of the diagnostic probe or be located within the device as part of the detection system, e.g. exposed to the dialysate at the outlet of a microdialysis probe.

Septum is a stopper made of natural or synthetic rubber-type material which can be pierced with a cannula or wire in a contamination-free and tight way. Only partial piercing with the tip of hollow needles or cannulas allows keeping the cannula tight and sterile during storage.

Skin attachment plate has preferentially a circular or oval footprint, is coated with an adhesive surface for attachment to the skin and has holes opposing the tips of the needles with sufficient diameter to allow an unhindered passage of the needles upon moving the skin attachment plate towards the needle support. The skin attachment plate is linked to the needle support by a retraction mechanism. The retraction mechanism is also ensuring a smooth and directionally guided movement, from a first position in which the skin attachment plate and the needle support are spaced from each-other so that the skin attachment plate is covering the tip of the needles, to a second position in which the skin attachment plate and the needle support are close to each-other, and the needles are protruding through the holes of the skin attachment plate.

In a preferred embodiment the skin attachment plate and the needle support are forming parallel planes and the retraction mechanism ensures a linear movement direction, guided e.g. by a sliding mechanism. The movement can be axial, i.e. 90° to the plane of the needle support and of the skin attachment plate or following a certain angle, e.g. 45°. The needles protruding from the needle support are fixedly positioned, preferentially parallel to the movement direction thus allowing the safe placement also of very thin needles of less than 0.3 mm diameter and minimizing invasiveness.

Alternatively, the skin attachment plate can be fixed at one locus of its periphery to the needle support by a hinge-type mechanism, the opposite part of the periphery being pushed away. In such an embodiment the movement of the skin attachment plate is arcuate with respect to the needle support and the needles have preferentially also a curved shape allowing to maintain an unchanged positioning of the needle entrance into the skin relative to the adhering skin attachment plate throughout the entire movement of the skin attachment plate towards the needle support.

The skin attachment plate can also be composed of two layers, a rigid layer facing the needle support and a flexible layer coated with the adhesive surface. Such a construction allows to deeply inserting the needles with a moderate overall hight of the skin insertion mechanism. The retraction mechanism is configured such that in the ready-to-use position both, the rigid and the flexible layers of the skin attachment plate are pushed away from the needle support and together cover the tip of the needles, and upon actuation of the retraction mechanism the rigid and the flexible layers of the skin attachment plate are shooting consecutively towards the needle support.

The holes in the skin attachment plate opposing the tips of the needles can house protecting septums of the cannulas or diagnostic probes which are pierced by the tips of the needles by the movement of the skin attachment plate against the needle support.

Sliding bolt mechanisms as a possible part of the release element adapts upon a linear or circular movement consecutively two or more fixed positions and consists of components which display a closed or open state, for example a solid surface or a hole. The movement of the sliding bolt mechanism is driven manually or by a mechanism, e.g. by a spring actuated by for example pressing or releasing a button, a handle, part of the device housing, or through a minimal turning movement. For inserting a flexible diagnostic probe within a guide needle by the skin insertion mechanism, movement of the sliding bolt mechanism upon an easy manipulation releases first the skin attachment plate from the ready-to-use position (position 1) to the next position (position 2) and inserts the guide needle into the skin. The interim blockage of the sliding bolt mechanism at position 2 is now released and allows to actuate the movement of the sliding bolt mechanism to the next position (position 3), which actuates the partial retraction or removal of the guide needle, leaving the active surface of the diagnostic probe exposed to subcutaneous tissue.

Withholding means are fixing e.g. a spring-type retraction mechanism in the ready-to-use, pre-stressed position and allow, actuated by the release element, a rapid release from this position in a coordinated way for all components of the retraction mechanism. The construction of the with-holding means and of the release element is complementary, e.g. the withholding means can consist of several pin-shaped elements protruding from the skin attachment plate and pushing onto a sliding bolt mechanism as release element, or the withholding means can consist of several hook-type components and the release element de-blocks these hook-type components by complementary pin-shaped elements, but other constructions using screws, ramps, levers etc. are also possible.

In the following preferred embodiments of the invention are described with reference to the accompanying drawings in which FIG. 1 is a diagrammatic sectional view of a skin insertion mechanism for perpendicular insertion of several, non-centrally positioned needles with an axially sliding spring-type mechanism according to one embodiment of the invention.

FIG. 3 is a diagrammatic sectional view of a skin insertion mechanism with a skin attachment plate which is composed of a rigid and a flexible layer.

FIG. 4 is a diagrammatic cross sectional view and sectional top view of a device for delivery of injection fluid through two consecutively activated cannulas inserted simultaneously according to one embodiment of the invention.

FIG. 5 is a diagrammatic cross sectional projected top view of a device for delivery of injection fluid through two consecutively activated cannulas inserted simultaneously according to an alternative embodiment of the invention.

Figure 1A:
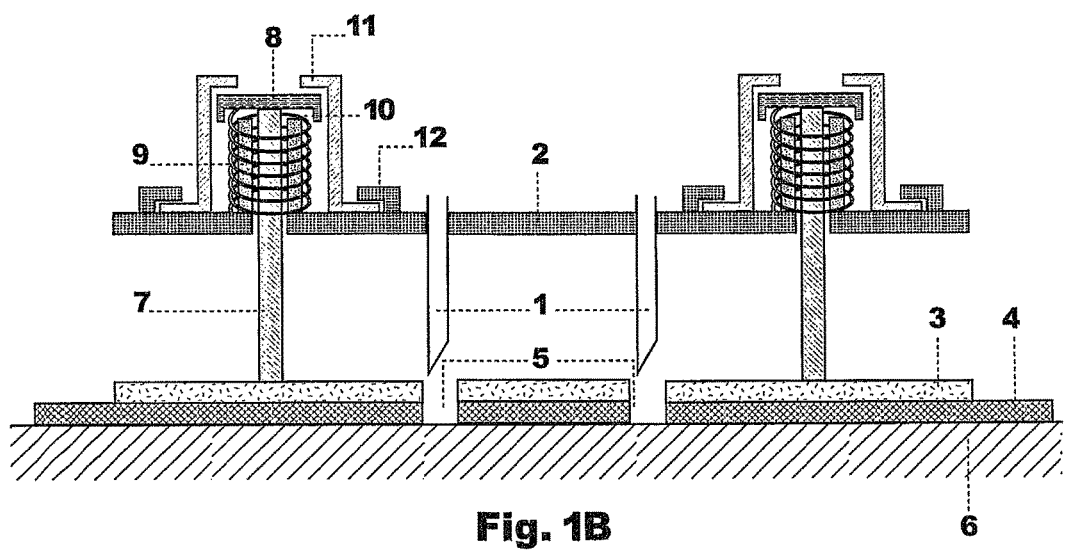
FIG. 1A shows the skin insertion mechanism in the ready-to-use position, FIG. 1B a sliding-bolt mechanism as release element and FIG. 1C the skin insertion mechanism in the operation mode following insertion of the needles into the skin.

FIG. 1A is a cross sectional view showing needles 1, which are fixedly positioned and hold perpendicularly by a needle support 2. A skin attachment plate 3 is coated with an adhesive layer 4 and has holes 5 opposing the tip of the needles. An individual's skin 6 is attached to the skin attachment plate 3 by an adhesive layer 4. A retraction mechanism consists in this embodiment of a spring-type mechanism comprising a telescopic guideways with an inner tube 7 fixed to the skin attachment plate and having a trip dog 8 at its other end. Tube 7 can slide within a shorter outer tube 9 fixed to the needle support to ensure a smooth and axially well-defined movement. Preferentially, one central or three to four such telescopic guideways distributed over the area of the attachment plate form the retraction mechanism.

FIG. 1A shows the skin insertion mechanism in the ready-to-use position. A pressure spring 10 is pre-stressed between the needle support 2 and the trip dog 8 which is held by withholding means 11 attached to the needle support 2 by a slot and key construction 12 ensuring that the skin attachment plate 3 is sufficienly spread away from the needle support 2 to conceal the needles 1 and protect them from contacting the skin 6 (position 1) even if the skin attachment plate is pushed manually against the skin of the individual for attaching the adhesive layer 4 to the skin.

Figure 1B:
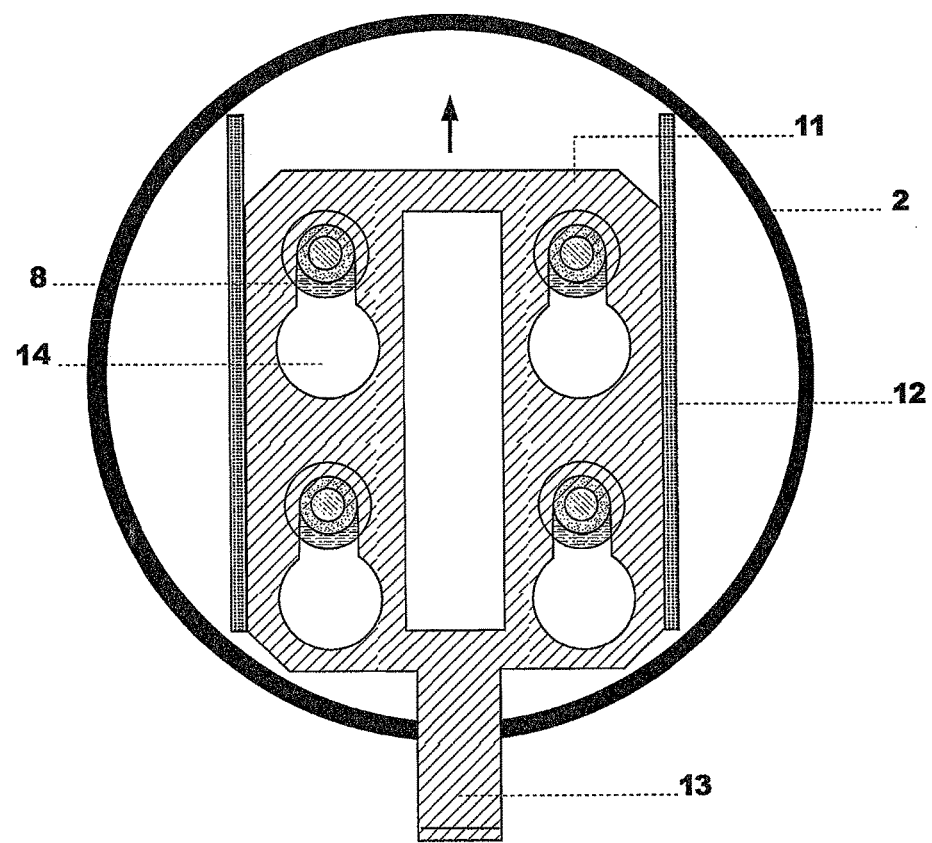
FIG. 1 shows a skin insertion mechanism for perpendicular insertion of several, non-centrally positioned needles according to one embodiment of the invention.

FIG. 1B shows in a diagrammatic sectional top view the withholding means 11 and the slot and key construction 12 forming the release element constructed as a sliding bolt mechanism. The withholding means 11 are constructed such that sliding in the horizontal direction indicated by an arrow and actuated by pressing a handle 13 of the withholding means 11 against the needle support 2 exposes holes 14 large enough to allow the passage of the trip dog 8. By this the spring 10 can relax from the pre-stressed position and the skin attachment plate 3 together with the skin 6 attached by the adhesive layer 4 is rapidly pulled against the needle support and the tip of the needles 1, with sufficient velocity and force for piercing the skin and completely inserting an implantable portion of the needles into the skin. The resulting operational position 2 is shown in FIG. 1C.

Figure 1C:
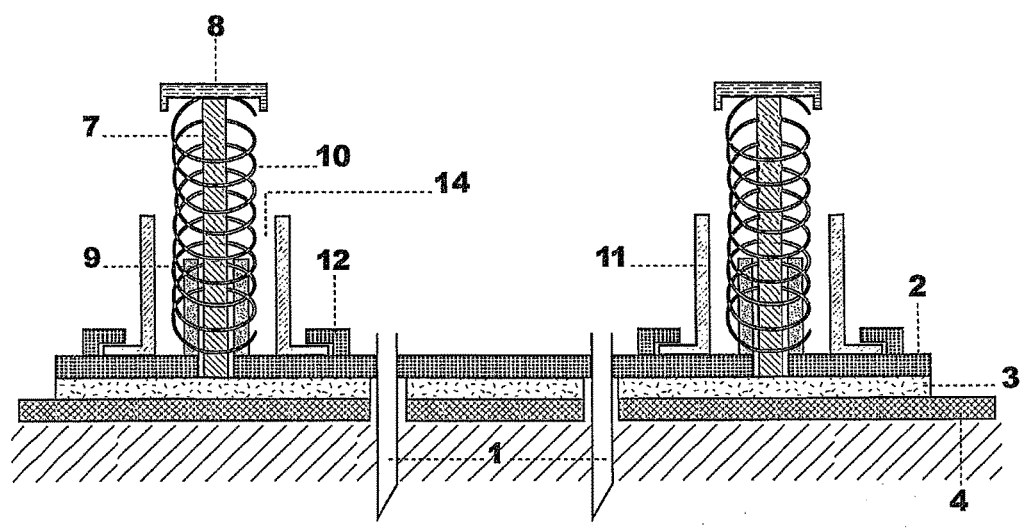

FIG. 1C shows the skin insertion mechanism in the operational position (position 2) in a cross sectional view. Sliding the withholding means 11 in the slot and key construction 12 in the horizontal direction exposed the holes 14 and the trip dog 8 has passed through these holes. Using the telescopic guideways for a well-defined axial movement, the relaxing spring 10 has pulled the inner tube 7 fixed to the skin attachment plate 2 by effecting its sliding within the outer tube 9 fixed to the needle support. By this movement the needle support 2, the skin attachment plate 3 with the adhesive layer 4 and the attached skin 6 are now stacked up and the implantable part of the needles 1 are inserted into the skin.

Alternatively, a construction can be chosen in which part of the retraction mechanism can be disconnected and removed following insertion of the needles into the skin. In order to reduce the volume and weight of the components remaining attached to the skin, such a construction is preferable if the skin insertion mechanism is used e.g. for an intradermal injection port, inserting the injection cannula into the skin and having a connecting element at the proximal end of the cannula, such as a septum or a connecting lock system, e.g. a Luer lock.

FIG. 2 shows the skin insertion mechanism integrated into the housing 15 of a device requiring needle insertion into the skin at an angle of 45°. The mechanism and construction is essentially similar to that shown in FIG. 1 for perpendicular needle insertion and the same numbering is used for similar elements. Since the needle support is in this embodiment fused with the housing 15 of a device, the telescopic guideways of the retraction mechanism and the needles 1 are fixed to this housing.

In contrast to the retraction mechanism shown in FIG. 1 the telescopic guideways have an outer tube 7 fixed to a skin attachment plate at an angle of 45° sliding over an inner tube 9 fixed at an angle of 45° to the housing 15 of the device ensuring the movement at an angle of 45°. A spring 10 in this embodiment is situated inside the inner tube 9 and is a pull-spring hauled between the skin attachment plate 3 and the housing 15. Withholding means 11 are constructed as a sliding bolt mechanism withholding the tube 7 attached to the skin attachment plate 3, against the pull of the spring 10. This withholding means 11 can be released by pressing a handle 13 against the housing 15.

Whereas in the embodiment depicted in FIG. 1 the adhesive surface 4 for attachment to the skin has a larger surface than the skin attachment plate 3, in the embodiment shown in FIG. 2 both have a similar surface but the adhesive surface 4 is fixed on the skin attachment plate 3 by a reduced surface, leaving an outer rim free, as shown in Detail A. Both designs prevent unintended detachment from the skin.

Figure 2A:
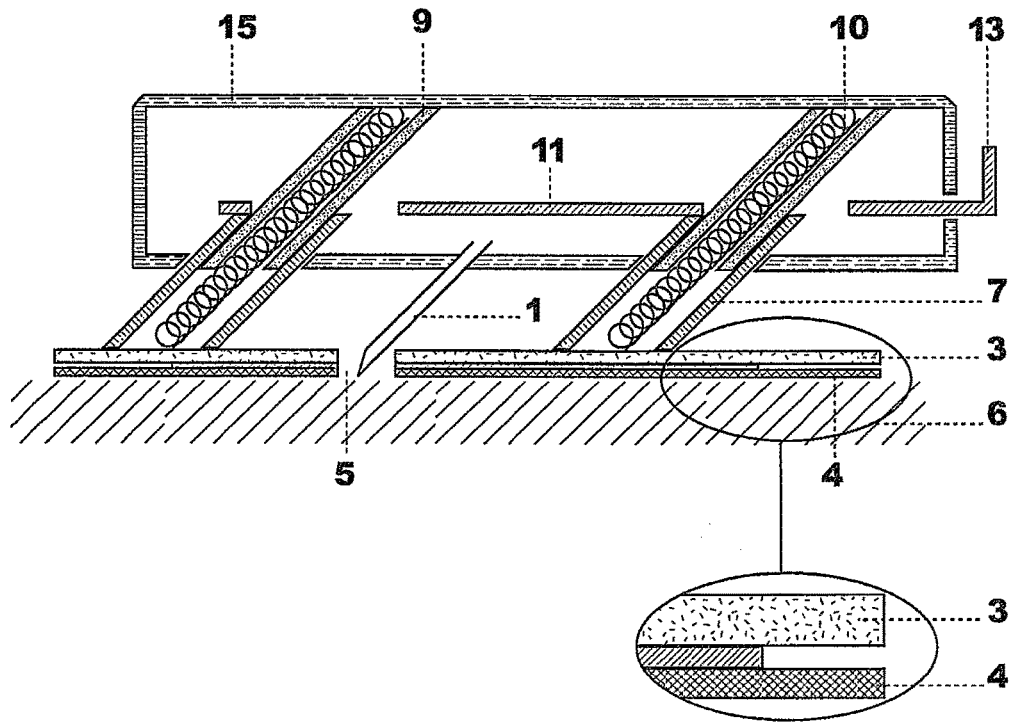
FIG. 2 is a diagrammatic sectional view of a skin insertion mechanism for insertion of a needle at 45° with a sliding spring-type mechanism according to an alternative embodiment of the invention.
Figure 2B:
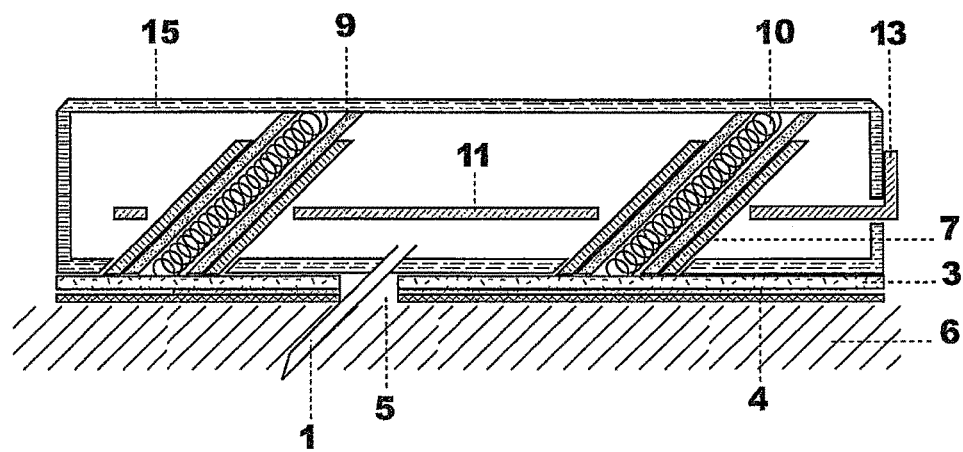

FIG. 2A shows the insertion mechanism of the device in the ready-to-use mode and FIG. 2B in the operation mode with the needle inserted at an angle of 45° into the skin. For better clarity, only one needle is shown and the functional elements connected to the needle are not shown, but this mechanism can also be used for the simultaneous insertion of several needles spread over the entire footprint of the device and having several functionalities.

FIG. 3 shows elements of a skin insertion mechanism related to the one shown in FIG. 1 but having a skin attachment plate which is composed of a rigid and a flexible layer. Such a construction is useful if a deep insertion of the needles is requested which surpasses the overall height of the device. For simplicity, only the left part of the cross sectional scheme is shown. A flexible part 17 of a skin attachment plate represents the left side of a cone with central hole, or of a gable with a central slit, or alternatively a flexible plate fixed at one locus of its periphery to the needle support with holes for passage of needles which are not centrally located.

FIG. 3A shows a diagrammatic sectional view of a skin insertion mechanism in the ready-to-use mode. By splitting the skin attachment plate into a rigid part 16 and a flexible part 17 which are both pushed away from the needle support 2, the additive distance to the needle support determines the overall needle insertion depth.

The needles 1 are covered and protected from touching the skin by the flexible part 17 which is coated with the adhesive layer 4. The retraction mechanism consists in this embodiment of two functional elements. A spring-type mechanism comprising a telescopic guideways and allowing the movement of the rigid part 16 of the skin attachment plate perpendicularly to the needle support similar to the mechanism shown in FIG. 1 is indicated only schematically by one inner tube 7 fixed to the skin attachment plate. The flexible part 17 of a spring-type material which is coated with the adhesive layer 4 represents the second functional element of the retraction mechanism. It is pre-stressed in the ready-to-use mode and bent away from the rigid part 16 of the skin attachment plate, concealing the tip of the needles. Withholding elements keeping the flexible part 17 pre-stressed can consist e.g. of several pin-shaped elements 18 protruding from the flexible part of the skin attachment plate and pushing onto the rigid part of the skin attachment plate with a hook-type construction 19. In the first step of the skin insertion process the retraction mechanism is actuated by a spring-type mechanism e.g. as described in FIG. 1 and the movement of the skin attachment plate against the needle support 2 is indicated by the arrow (a).

FIG. 3B shows an intermediary stage of the needle insertion process into the skin in which the rigid layer 16 of the skin attachment plate has almost reached the needle support 2. At this stage, the flexible layer 17 of the skin attachment plate is still bent away from the rigid layer 16 by the hook-type construction 19 of the pin-shaped elements 18. Pulling the skin attached by the adhesive layer 4 against the tip of the needles 1 effects the piercing of the skin 6 but only a first part of insertion of the implantable part of the needles into the skin. Further movement of the skin attachment plate towards the needle support 2, indicated by the arrow (a), effects the passage of the extended bevel 20 of the pin-shaped withholding elements 18 through an opening of the needle support 2, and by this the bending of the withholding elements 18 in the direction of the arrow (b). This bending releases the hook-type construction 19 and the flexible layer 17 of the skin attachment plate can shoot from its pre-stressed, bent form in the direction of the arrow (c), pulling the skin attached by the adhesive layer towards the needle support.

FIG. 3C shows the final position of the skin insertion mechanism in the operation mode. The rigid layer 16 and the flexible layer 17 of the skin attachment plate are together and firmly stacked up with the needle support 2 and fixed together by a hook 21. The skin 6 is attached by the adhesive layer 4 and the implantable part of the needles 1 is entirely inserted into the skin.

FIG. 4 shows an injection device with two injection cannulas linked to a single syringe pump being actuated sequentially. For simultaneous insertion of both cannulas being located close to the periphery of the device at a radial angle of less than 90° an alternative embodiment of the invention is shown in which the skin attachment plate is fixed at one locus of its periphery to the needle support by a hinge-type mechanism. Such a construction allows using a very simple retraction mechanism without the need for special guideway mechanisms for ensuring a well-defined movement since the hinge-type mechanism attaching the skin attachment plate to the needle support guides the arcuate movement.

FIG. 4A shows a cross-section of the device in the ready-to-use position. A needle support 2 is integrated into a casing 15. A skin attachment plate 3 coated with an adhesive layer 4 is linked to a needle support 2 by a hinge-type mechanism 22. A retraction mechanism consists in this embodiment of a spring-type mechanism comprising a pull-spring 10 hauled between the skin attachment plate 3 and the housing 15. Against the pull-force of the spring, the skin attachment plate 3 is spread away from the needle support 2 by withholding means consisting of a pressure-pin 23 attached to the skin attachment plate 3 and a flexible holding-back element 24 having a catch, which can be disengaged by pressing a release knob 25 which is sliding in a guideways 26. Pressing the release knob 25 releases the spring and results in an arcuate movement of the skin attachment plate 3 against the needle support 2 as indicated by the arrow, with the hinge-type mechanism 22 as pivot. By this movement the skin 6 attached to the skin attachment plate 3 by an adhesive 4 is rapidly pulled against the tip of the cannulas 1 and the implantable part of the needles gets inserted into the skin. It is advantageous if the needles 1 and the pressure-pin 23 are bent according to the radius of the arcuate movement.

FIG. 4B shows a projected top view of the device with a syringe-type pump 27 having a piston 28 driven by a gear train 29 and a motor 30, under the control of control elements 32. The outlet of the syringe is split, ending in two delivery cannulas 1 and 1' which are actuated sequentially by valves 31 and 31'. By this, a granulomatous response to the injection fluid at the injection site can be avoided, allowing the use of the device for an extended infusion time. For high precision of delivery combined with a small footprint of the device, preferentially a circular syringe pump with a toroidal barrel can be used, as shown in FIG. 5.

FIG. 5 shows the projected top view of an injection device with a circular syringe-type pump. This injection device with two injection cannulas linked to a single circular syringe pump has essentially similar features as the one described in FIG. 4; in particular it has also the same skin insertion mechanism for the cannulas and therefore only the elements different from the ones in FIG. 4 in this embodiment are shown.

An arcuate barrel 33 of the circular syringe pump has the form of a segment of a toroidal tube. A piston 34 is arranged in the interior of the barrel and is provided with a seal 35 fitting tightly at the inner wall of the barrel. The piston is connected to a driving rod 36 which is circularly shaped for driving the piston through the entire length of the barrel. The driving rod 36 of the piston is formed preferentially in such a way that its movement is guided and supported by the inner surface of the barrel wall, e.g. by a brace 37 of optimized form and material for even movement with low friction.

The inner side of the rod has a gear rim 38 which is driven by a gear drive 39. The gear drive is driven e.g. by a gear train and an electrical motor (not shown). Two cannulas are connected perpendicularly to the barrel, a first cannula 40 in the middle of the barrel and a second cannula 41 to the end piece 42 of the barrel. For the sequential actuation of the two injection fluid delivery cannulas in this embodiment a solution with simple, only mechanical components is shown which also avoids the need for connecting tubes or long channels between barrel outlet and the cannulas. Such a construction is not only simpler and avoiding potential connection problems but is also less prone to the well-known problems with air bubbles in connecting lines and valves, thus resulting in an overall more robust and safer injection device.

As shown in Detail A, the end piece 42 of the barrel the short connecting channel 43 to the second delivery cannula 41 houses a movable stopper 44 which in a first position prevents flow of injection fluid from the barrel. In this stage fluid delivery takes place only through the first cannula 40 until about half of the total delivery volume is injected. Once the piston 34 gets close to the barrel outlet through this first cannula the stopper 44 is pulled back at its handle 45 by a lever system 46, opening free flow from the barrel to the injection cannula 41. When the the piston 34 has passed the barrel outlet to the first cannula 40, delivery of injection fluid through this first cannula stops automatically, resulting in a consecutive delivery of injection fluid through cannula 40 and 41 with a short overlap.

A solution for the actuation of flow through the second cannula 41 by the lever system 46 comprises a buffer 47 fixedly mounted on the driving rod 36 which pushes the lever system in clockwise direction indicated by arrows but only for a short move sufficient for opening the connecting channel 43 to the second delivery cannula 41 by pulling the stopper 44 back behind the exit of the channel to the cannula 41 but still making the channel leak-proof. As shown in Detail B this can be achieved e.g. by a construction using a spring-type arm 48 of the lever system 46 which is held stressed on a stand 49 and relaxes falling down from the stand once the buffer 47 has pushed the spring-type arm 48 of the lever system over the edge of this stand, as indicated by the arrow.

Detail A further indicates the possibility to use the movement of the skin attachment plate 3 against the needle support 2 for opening a seal at the tip of the cannula 41 (and 40, not shown in this Detail A). By the movement of the skin attachment plate against the tip of the cannula by the skin insertion mechanism, indicated by the arrows, the septum 50 protecting and keeping closed the cannula is being pierced and pushed against a recess 51 in the needle support. Alternatively, instead of a septum, a closed tube of thin wall covering the entire implantable part of the cannula can be used. Such a simple constructive element allows keeping the injection fluid and cannula sterile and free of air bubbles during storage and does not require additional manipulation by the user for removal of the cannula seal.

FIG. 6 shows a cross-sectional view of a device with multiple needles with multiple functions inserted simultaneously into an individual's skin according to one embodiment of the subject invention. Multiple needles with several functions might be needed e.g. for delivery of injection fluid under the control of the simultaneous determination of analytes by means of diagnostic probes housed by the same device. For the periodic in situ calibration of the diagnostic probes a separate cannula delivering a calibration fluid might be needed and in addition needles as probes transmitting signals might be necessary to notify the patient in case of problems requiring intervention. The exemplified device could represent an embodiment representing a closed-loop system for tight glycemic control in diabetic or critically ill patients.

Figure 6A:
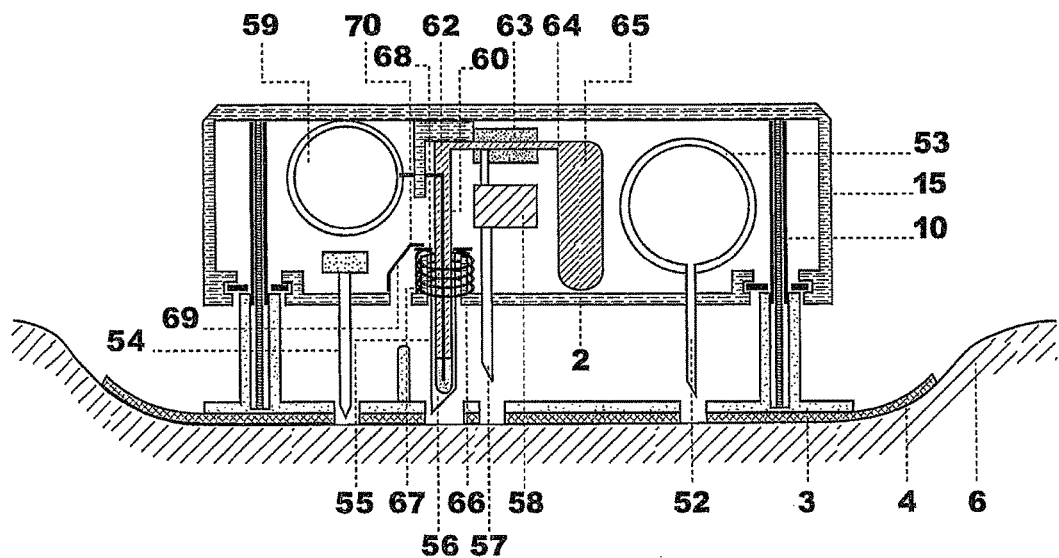
FIG. 6 is a diagrammatic cross sectional view of a device for delivery of injection fluid, having a sensor inserted within a guide needle, and probes for transmitting signals subcutaneously inserted simultaneously according to one embodiment of the invention.

FIG. 6A shows the device in the ready-to-use position pressed against the skin, thus forming an impression of the skin and ensuring a firm attachment of an adhesive surface 4 of a skin attachment plate 3 to the skin 6. The skin 6 is attached to the skin attachment plate 3 by an adhesive layer 4. Needle 52 is a cannula connected to an injection fluid pump 53; needles 54 represent probes transmitting signals. A diagnostic probe 55 in the shown example is a microdialysis probe, being representative of diagnostic probes having a flexible structure and therefore needing a guide needle 56 for insertion into the skin. Alternatively, the diagnostic probe 55 could be a sensor on a flexible support with an active surface at its tip. Needle 57 is a cannula connected to a pump for delivery of a calibration fluid from a delivery pump system 58 for in situ calibration of the diagnostic probe. A needle support 2 is integrated into a casing 15 and needles 52, 54, and 57 as well as a diagnostic probe 55 are fixedly attached to the needle support/casing. A microdialysis probe 55 is linked to a pump 59 delivering dialysis fluid through a central tube 60 to an active, semipermeable surface 61 and has an outlet 62 of the peripheral dialysate collecting tube linked to a flow-through analyte determining system 63 with an outlet 64 to a waste collecting receptacle 65. Pump drive systems and the control means are not shown.

The analyte determining system 63 may further comprise means for determination of microdialysis recovery e.g. a sensing system measuring the residual concentration of an indicator substance contained in the dialysis fluid. If the molecular weight of this indicator substance is close to the molecular weight of the analyte, the magnitude of decrease in concentration of the indicator substance can be considered as indicative of the microdialysis recovery of the analyte.

A retraction mechanism for pulling the skin attachment plate 3 with the attached skin 6 against the needle support 2 consists of a spring-type mechanism essentially similar to the one discussed in FIG. 1 but the spring 10 in this embodiment is a pull-spring hauled between the skin attachment plate 3 and the housing 15. The retraction mechanism can be released by a release element which can be e.g. analogous to the ones discussed in FIGS. 1 to 4 (only schematically depicted in this figure). The guide needle 56 can slide back along the diagnostic probe 55 actuated by a pressure spring 66 and guiding means 67 ensuring a smooth and axially well-defined movement. In the ready-to-use position shown in FIG. 6A it is fixed relative to the needle support 2 by a withholding mechanism against the push-force of the spring 66, consisting e.g. of a withholding flage 68 at the end of the guide needle 56 and a holding-back element 69 having a catch 70.

Figure 6B:
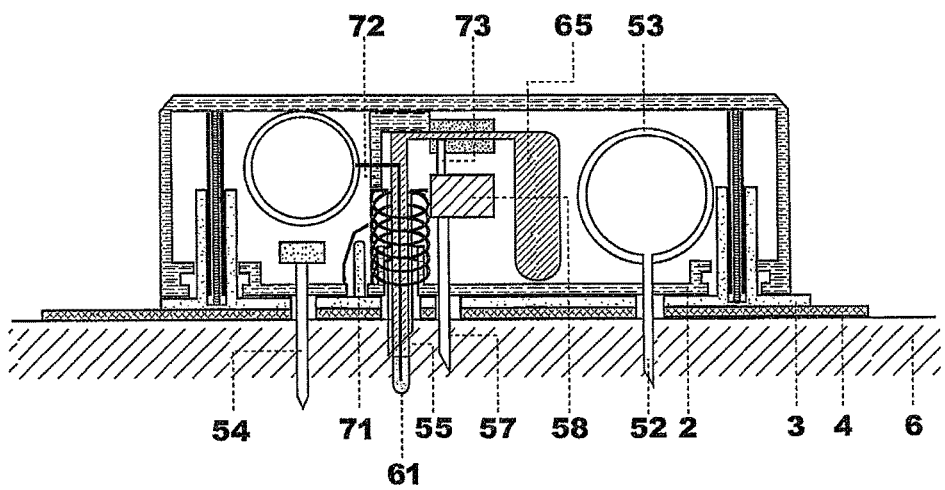

FIG. 6B shows the device in the operation mode, after actuation of the skin insertion mechanism. Upon release of the retraction mechanism the skin attachment plate 3 with the adhesive layer 4 and the attached skin 6 have been pulled against the needle support 2 and are now stacked up. The implantable part of the needles has been inserted into the skin. Movement of the skin attachment plate 3 against the needle support 2 has also disengaged the withholding flage 68 of the guide needle of the diagnostic element 56 by bending-back the holding-back element 69 by way of pressure pins 71, which are fixed on the skin attachment plate, and the guide needle of the diagnostic element 56 has been partially retracted by the release of the spring 66 from its pre-stressed state, the end position being defined by a bumper 72. This mechanism ensures that the guide needle with the diagnostic element is inserted into the skin before partial retraction of the guide needle is actuated. As the diagnostic element 56 is fixedly positioned relative to the casing 15, the active, semi-permeable surface 61 which is close to the tip, is after partial retraction of the guide needle exposed to subcutaneous tissue. This partial retraction of the guide needle can occur without interfering with the connections to the pump 59 and the analyte determining system 63.

Alternative methods described in prior art, e.g. in WO 03/055540 A1 for microdialysis probes, remove the guide cannula by withdrawal in a proximal direction upon insertion of the probe but the proximal ends of the flexible connecting tubes have to be attached to the dialysis pump thereafter. Alternatively U-shaped guide needles with a longitudinal slit are used, which allow removal of the guide needle without interference with connections. Both these methods have serious limitations for miniaturization. In contrast, the partial retraction of the guide needle by a mechanism ensuring that this takes place strictly consecutively to guide needle insertion into the skin exposes the active surface of the diagnostic probe to subcutaneous tissue, but does not interfere with the connections to the pump 59 and to the analyte determining system, allows miniaturization, and in addition is easier and safer to use than removal of the guide needle.

Periodic calibration of the diagnostic probe can be done in-situ by delivery of a calibration fluid from a delivery pump system 58 through the cannula 57 having its outlet close to the active surface of the diagnostic probe. Alternatively, the calibration fluid can be delivered directly to the flow-through analyte determining system 63 through a connection 73.

In case of in-situ delivery of a calibration fluid it might be necessary to have a tandem system distantly located from each-other and alternatingly being in calibration mode, in order to secure continuous reliable analyte determination, without interruption by calibration and re-establishment of the physiological analyte concentration in the subcutaneous tissue by diffusion of the calibration fluid away from the active surface. Such a system might be e.g. necessary for reliable tight glycemic control in intensive care or diabetic patients.

It is also possible instead of a pump system to use for the periodical calibration a simple manual system operated by the patient by pressing a knob or handle resulting in the delivery from e.g. a resevoir bag or a syringe a portion of calibration fluid. The principles for the construction of such delivery mechanisms manually operated by pressing on a knob or handle-type actuation interface for repetitive delivery of several equal portions of fluid from a reservoir are well known in drug delivery, e.g insulin pens, or laboratory devices or even household articles.

FIG. 7 is a diagrammatic cross sectional view of a skin insertion mechanism for the cannula of an infusion set according to one embodiment of the invention which allows avoiding the manual insertion of the cannula into the skin. Such an insertion mechanism is not only overcoming the psychological hurdle of handling a needle and manually inserting it into the skin but is also less painful and safer, since needle insertion takes place at a defined and high velocity, unlike the big variations and holding-back attitude if needle insertion is done manually by the patient.

Following needle insertion most elements of the insertion mechanism can be removed for easy connection to a pump system and allowing keeping the actual infusion port attached to the skin during administration of the infusion fluid very small causing minimal discomfort. FIG. 7 describes one possible constructional solution allowing these functions but many alternative constructional elements are also possible.

Figure 7A:
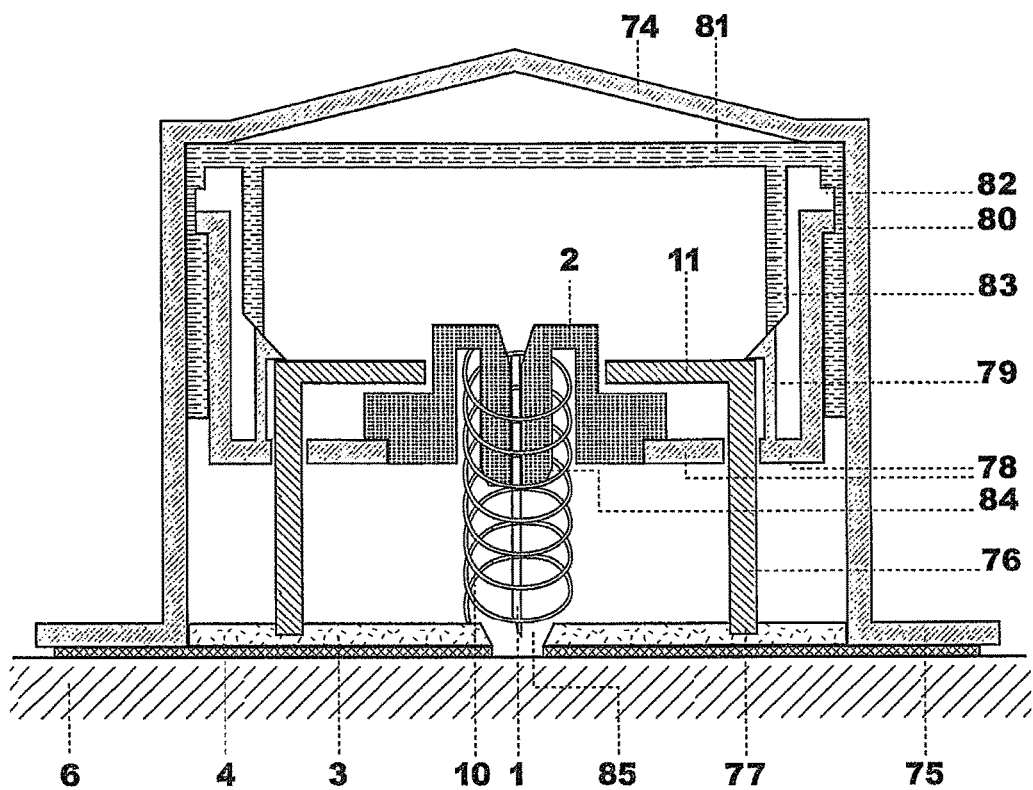
FIG. 7 is a diagrammatic cross sectional view of a skin insertion mechanism for the cannula of an infusion set according to one embodiment of the invention.

FIG. 7A shows the skin insertion mechanism in the ready-to-use position applied with a functional package 74 onto the skin, after a cover foil keeping sterility during storage has been removed from the bottom of the package together with the cover foil protecting an adhesive (not shown). In the functional package 74 the release element is protected from unintended actuation and a rim 75 of the package helps the firm attachment to the skin 6 by pressing the adhesive layer 4 all around. After attachment to the skin the functional package 74 can be removed.

The needle support 2 is attached to the skin attachment plate 3 by a stretched pull-spring 10 and the withholding means 11 with several, preferentially 3 to 6 pin-shaped elements 76 are ensuring that the skin attachment plate 3 is sufficiently spread away from the needle support 2 to conceal the cannula 1 and protect it from contacting the skin (position 1). The withholding means 11 is reversibly linked to the needle support 2 through a linking component 78.

Figure 7B:
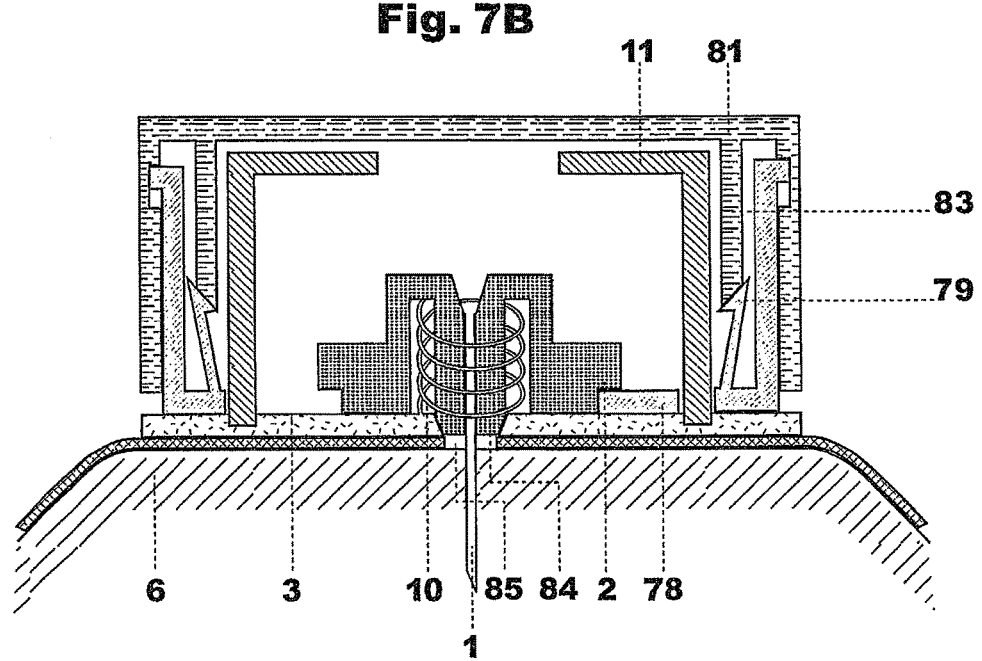
Figure 7C:
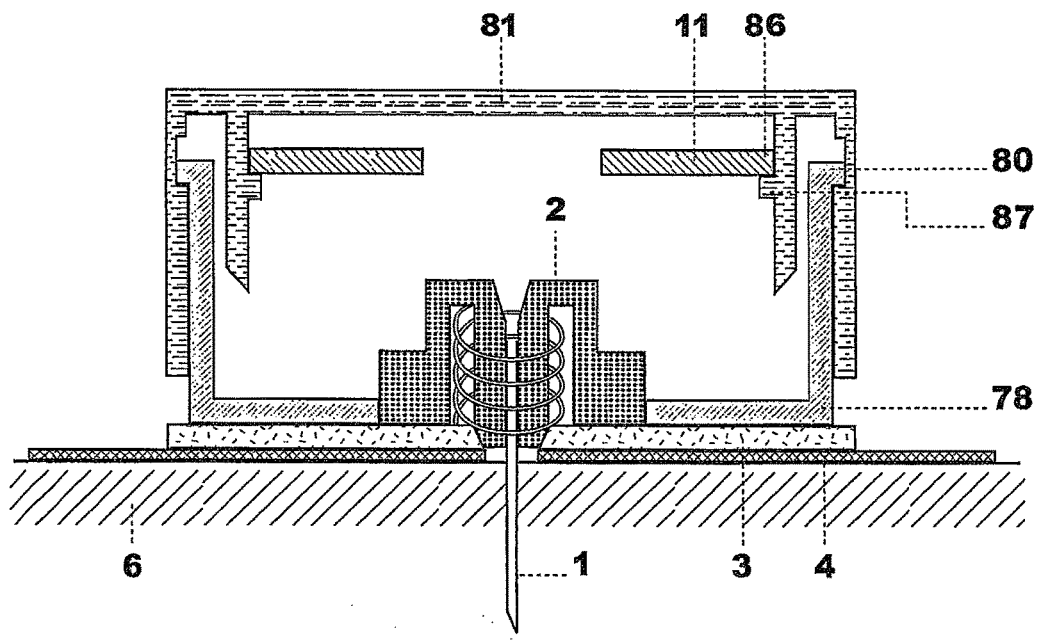

In this embodiment of the invention the needle support 2 has tooth-like, preferentially 3 to 6, radial protrusions allowing not only an easy mounting of the pull-spring 10 but also engaging with a linking component 78 only at the periphery of these protrusions allowing a dis-engagement upon rotational movement of the linking component 78 relative to the needle support (as shown in FIG. 7C), but several other constructions allowing dis-engagement are also possible. The linking component 78 has hook-type elements 79 and a catch mechanism 80 linking it to a cover 81 e.g. in an axial groove 82 in such a way that a limited axial but no rotational movement of the cover 81 against the linking component 78 is possible. The cover 81 has also protruding wedge-shaped elements 83 set against a wedge surface of the hook-type elements 79.

FIG. 7B depicts the situation following pushing the cover 81 (position 2). The wedge-shaped elements 83 have bent the hook-type elements 79 radially, thus dis-engaging them from the withholding means 11. This has released the withholding means 11 and the stretched spring 10 has pulled the skin attachment plate 3 with the attached skin 6 against the needle support 2 effecting the insertion of the cannula 1 into the skin. A conical protrusion 84 of the needle support firmly attaches into a conical hole 85 in the skin attachment plate, but alternatively also e.g. hook-type elements can be used for linking the two together.

Figure 7D:
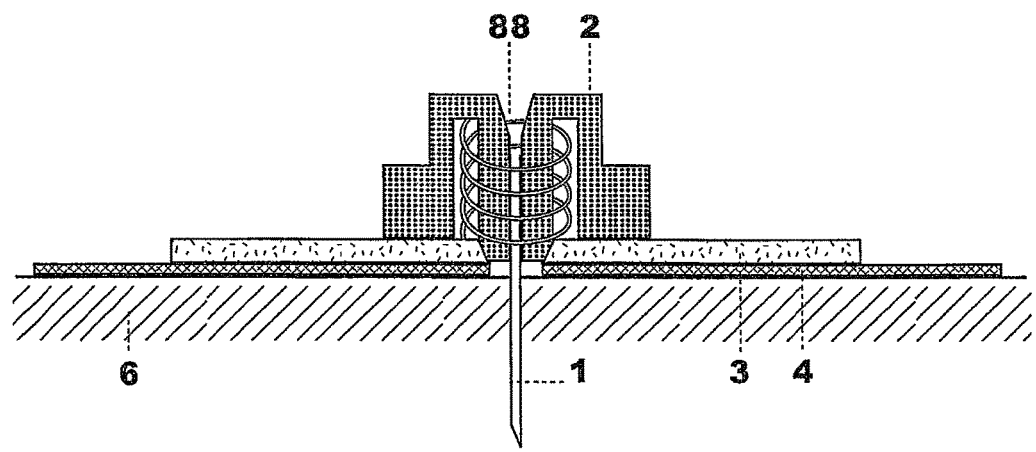

Following, insertion of the cannula into the skin most elements of the insertion mechanism can be removed by slight rotational movement of the cover 80 and lifting it off with the attached elements, as depicted in FIGS. 7C and 7D.

FIG. 7C shows a diagrammatic cross section following a slight rotational movement of the cover 81 respective to the skin attachment plate 3. The cross-sectional plane in this figure is slightly different from the one shown in FIGS. 7A and 7B, turned to be between the tooth-like radial protrusions of the needle support 2, illustrative of the situation allowing dis-assembly of part of the skin insertion mechanism. The slight rotational movement of the cover 81 with the attached linking component 78 respective to the skin attachment plate 3 results in a dis-engagement between the needle support 2 and the linking component 78. In addition, protrusions 86 of the withholding means 11 engage with protrusions 87 linking the withholding means 11 to the cover 81. Since the catch mechanism 80 keeps the linking component 78 and the cover 81 together, lifting off the cover removes also the linking component 78 and the with-holding means 11.

FIG. 7D shows the infusion port attached to the skin during administration of the infusion fluid following removal of most elements of the insertion mechanism. The connecting element 88 of the needle support 2, e.g. a Luer lock-type conical hole or a septum, is now freely accessible for a corresponding connective element of a tube allowing linking to a pump system.

Upon reading these specifications, various alternative embodiments will become obvious to the skilled artisan. For example, a subcutaneous access device according to the subject invention can be also used for skin insertion of a cannula of a single-use syringe or pen and be combined with mechanisms for needle retraction and protection after use as known in prior art for such systems. For example, the retraction mechanism of the skin attachment plate or the release element can be electromagnetic, piezoelectric, pneumatic, etc. and the needles inserted into the skin can be any kind of pin or hollow needle with all types of functions requiring subcutaneous access.

The major advantages of a skin insertion mechanism of needles described above are that the connections to the functional elements of the device having such a skin insertion mechanism have not to be flexible or manually established after skin insertion but can be manufactured as rigid connections, offering superior safety of operation and improved possibilities for miniaturization. Further, the danger that a needle is causing only an indentation of the skin rather than piercing and implantation is essentially eliminated by the forced movement of the attached skin against the needle. In addition, a number of needles with different functionalities can be inserted simultaneously sharing the same insertion mechanism and the location of these needles can be at any location of the skin contact surface of the device. There is also no limitation to the insertion depth and angle: the height and footprint of the device can be kept relatively small even for deep insertion. Moreover, it is also possible to reliably insert the needles with a low insertion depth, or pairs or arrays of needles at a close and well-defined distance from each other by the precise holding of the skin around the needle and high velocity by pulling the skin against the tip of the cannula avoiding that impression of the skin is taking place, leading to unreliable piercing and insertion depth.

The invention claimed is:

1. A device for subcutaneous access adapted to insert a needle into an individual's skin by effecting a relative movement between a surface of the skin and the needle, the device comprising:
   a device body, including a needle support, and the needle is fixedly held by the needle support in the device body;
   a skin attachment plate, including an adhesive surface adapted for attachment to the skin, the skin attachment plate being placed between the device body and the skin, and the device body and the skin attachment plate being movable relative to one another by linear guideways, with one end of the linear guideways being fixedly connected to the skin attachment plate and another end of the linear guideways being movably connected to the device body; and
   the linear guideways, the linear guideways including inner tubes connected to the skin attachment plate, the inner tubes being telescopically slidable in outer tubes that are connected to the device body, and the linear guideways being provided with retraction mechanisms, the retraction mechanisms being spring-type mechanisms arranged between the skin attachment plate and the movable end of the linear guideways and configured such that in a ready-to-use position, with the skin attachment plate spaced from the device body, the spring-type mechanisms are held pre-stressed by a withholding mechanism and, actuated by a release element, shoot into a relaxed state so that the device body with the fixedly held needle and the skin attachment plate move towards one another.

2. The subcutaneous access device according to claim 1, wherein in the ready-to-use position the skin attachment plate is pushed away from the needle support and shields a tip of the needle, and upon actuation of the retraction mechanism, effects subcutaneous insertion of the needle by the tip of the fixedly held needle and the skin, which is attached by the adhesive surface, moving towards one another.

3. The subcutaneous access device according to claim 1, wherein the release element comprises a sliding bolt mechanism actuated by pressing a handle or knob.

4. The subcutaneous access device according to claim 1, wherein the skin attachment plate is attached to the needle support by a sliding mechanism, keeping the skin attachment plate and the needle support parallel in the ready-to-use position and throughout movement relative to each-other.

5. The subcutaneous access device according to claim 1, wherein the skin attachment plate is attached to the needle support by an axially sliding mechanism.

6. The subcutaneous access device according to claim 1, wherein the skin attachment plate is attached to the needle support by a linearly sliding mechanism at an angle different from axial.

7. The subcutaneous access device according to claim 1, wherein the skin attachment plate is fixed at one locus of its periphery to the needle support by a hinge-type mechanism, an opposite part of the periphery being pushed away from the needle support against pull-back of a spring-type mechanism thereby shielding a tip of the fixedly held needle.

8. The subcutaneous access device according to claim 1, wherein multiple needles are held in the needle support for simultaneous insertion into the skin.

9. The subcutaneous access device according to claim 1, wherein the skin attachment plate includes a rigid layer and a flexible layer coated with the adhesive surface.

10. The subcutaneous access device according to claim 9, wherein the retraction mechanism is configured such that in the ready-to-use position, both the rigid and the flexible layers of the skin attachment plate are pushed away from the needle support and together shield a tip of the needle, and upon actuation of the retraction mechanism, the rigid and the flexible layers of the skin attachment plate shoot consecutively towards the needle support.

11. The subcutaneous access device according to claim 1, wherein the adhesive surface adapted for attachment to the skin is fixed on the skin attachment plate by a reduced surface in comparison to the adhesive surface attached to the skin.

12. The subcutaneous access device according to claim 1, wherein the retraction mechanisms are partially removable after skin insertion of the needle.

13. The subcutaneous access device according to claim 1, further comprising a single pump and a mechanism to consecutively open and close multiple needles, wherein for subcutaneous delivery of an injection fluid into a patient, the multiple needles are connected to the single pump for sequential actuation and the mechanism to consecutively open and close the needles.

14. The subcutaneous access device according to claim 1, further comprising a sensor to determine subcutaneous analyte levels.

15. The subcutaneous access device according to claim 14, wherein the sensor to determine subcutaneous analyte levels includes analyte determining systems comprising needles formed as diagnostic probes to contact the subcutaneous tissue.

16. The subcutaneous access device according to claim 15, wherein the sensor to determine subcutaneous analyte levels includes a calibration system to periodically calibrate the analyte determining systems.

17. The subcutaneous access device according to claim 16, wherein the calibration system comprises a delivery system with a cannula inserted into the skin together with the diagnostic probes to deliver calibration fluid to a vicinity of an active surface of the diagnostic probes in situ.

18. The subcutaneous access device according to claim 1, further comprising at least one delivery system for different functions that comprises circular syringe pumps.

19. The subcutaneous access device according to claim 1, wherein an insertion mechanism actuates piercing of a protecting septum covering a tip of the needle before insertion into the skin.

20. The subcutaneous access device according to claim 1, wherein the device is comprised in a functional package including a rim to press an outer rim of the adhesive layer towards the skin and protecting the release and actuation elements of the device against unintended activation.

\* \* \* \* \*